(12) United States Patent
Kandula

(10) Patent No.: US 8,871,805 B2
(45) Date of Patent: Oct. 28, 2014

(54) COMPOUND, COMPOSITION AND USES THEREOF

(71) Applicant: Mahesh Kandula, Andhra Pradesh (IN)

(72) Inventor: Mahesh Kandula, Andhra Pradesh (IN)

(73) Assignee: Krisani Biosciences Pvt. Ltd., Hyderabad, Andhra Pradesh (IN)

( * ) Notice: Subject to any disclaimer, the term of this patent is extended or adjusted under 35 U.S.C. 154(b) by 0 days.

(21) Appl. No.: 13/858,045

(22) Filed: Apr. 6, 2013

(65) Prior Publication Data
US 2013/0225680 A1 Aug. 29, 2013

Related U.S. Application Data

(63) Continuation of application No. 13/649,094, filed on Oct. 10, 2012, now Pat. No. 8,445,707, and a continuation of application No. 13/152,864, filed on Jun. 3, 2011.

(30) Foreign Application Priority Data

Sep. 24, 2012 (IN) .............................. 3947/CHE/2012
Oct. 9, 2012 (WO) .................. PCT/IN2012/000668

(51) Int. Cl.
*A61K 31/21* (2006.01)
*C07C 233/00* (2006.01)
*C07C 327/30* (2006.01)
*C07C 321/10* (2006.01)
*C07C 323/41* (2006.01)
*C07C 321/20* (2006.01)

(52) U.S. Cl.
CPC ............. *C07C 327/30* (2013.01); *C07C 321/10* (2013.01); *C07C 323/41* (2013.01); *C07C 321/20* (2013.01)
USPC .................................. 514/513; 554/35; 554/42

(58) Field of Classification Search
CPC ....................................................... C07C 233/00
USPC ....................................... 554/35, 42; 514/513
See application file for complete search history.

(56) References Cited

U.S. PATENT DOCUMENTS

2010/0303870 A1* 12/2010 Dohil et al. ................... 424/400

* cited by examiner

*Primary Examiner* — Deborah D Carr
(74) *Attorney, Agent, or Firm* — Raj Abhyanker, P.C.

(57) ABSTRACT

The disclosure herein provides the compounds of Formulas 1 and its pharmaceutical acceptable salts, as well as polymorphs, solvates, and hydrates thereof. These salts may be formulated as pharmaceutical compositions. The pharmaceutical compositions may be formulated for oral administration, transdermal administration, and/or injection. Such compositions may be used for the treatment of metabolic conditions, cystinosis, non-alcoholic Steatohepatitis, hypertriglyceridemia, and/or neurodegenerative disorders, and/or their associated complications.

3 Claims, 7 Drawing Sheets

PARAMETER ESTIMATES FROM MEAN PLASMA AND BRAIN CONCENTRATION DATA OF KB-ND-002, CYSTEAMINE HYDROCHLORIDE AND EPA.

| MATRIX | TREATMENT (GROUP) | DOSE (MG/KG) | CMAX (NG/ML) | CMAX/D (NG/ML)/ (MG/KG) | TMAX (H) | AUC(0-T) (NG.H/ML) | AUC(0-T)/D (NG.H/ML)/ (MG/KG) | AUC(0-INF) (NG.H/ML) | AUC(0-INF)/D (NG.H/ML)/ (MG/KG) | T1/2 (H) | Rsq |
|---|---|---|---|---|---|---|---|---|---|---|---|
| PLASMA | KB-ND-002 (GROUP 1) | 60 | 318 | NC | 5.00 | 806.6 | NC | NC | NC | NC | NC |
| | KB-ND-002 (GROUP 2) | 112 | 244 | NC | 0.25 | 724.6 | NC | 4403 #^o~+ | NC | 16.17 #^o~+ | 0.11 |
| | KB-ND-002 (GROUP 3) | 225 | 150 | NC | 0.25 | 653.1 | NC | 2319 *#o | NC | 9.25 *#o | 1.00 |
| | CYSTEAMINE (GROUP 4) | 112 | 173 | NC | 0.50 | 628.1 | NC | 1577 #o~+ | NC | 6.52 #o~+ | 0.26 |
| | EICOSAPENTANO-IEC ACID (GROUP 5) | 112 | 2440 | 21.8 | 1.00 | 3276 | 29.25 | 4715 #o~+ | 42.10 #o~+ | 3.27 #o~+ | 0.73 |
| BRAIN | KB-ND-002 (GROUP 1) | 60 | 810 | NC | 0.50 | 3773 | NC | 36940 #o | NC | 32.09 #o | 0.85 |
| | KB-ND-002 (GROUP 2) | 112 | 808 | NC | 4.00 | 3819 | NC | NC | NC | NC | NC |
| | KB-ND-002 (GROUP 3) | 225 | 781 | NC | 3.00 | 3683 | NC | 30630 *#o~+ | NC | 25.27 *#^o~+ | 0.67 |
| | CYSTEAMINE (GROUP 4) | 112 | 833 | NC | 5.00 | 3942 | NC | NC | NC | NC | NC |
| | EICOSAPENTANO-IEC ACID (GROUP 5) | 112 | 1110 | 9.93 | 1.00 | 4672 | 41.71 | NC | NC | NC | NC |

* < 4 DATA POINTS USED TO DETERMINE TERMINAL ELIMINATION SLOPE; # THE TERMINAL ELIMINATION SLOPE COVERED < 2 HALF-LIVES (T1/2 AS DETERMINE BY THE REGRESSION); ^CMAX INCLUDED AS THE FIRST POINT OF THE TERMINAL ELIMINATION SLOPE; ° THE AUC EXTRAPOLATED > 20%; ~ THE REGRESSION LINE FITTED TO THE TERMINAL ELIMINATION PHASE DATA IS OF POOR FIT (Rsq < 0.80), = ESTIMATION OF TERMINAL ELIMINATION PHASE SLOPE BY WINNONLIN CONSIDERED BY PHARMACOKINETICIST TO BE UNRELIABLE; AUC(0-INF), AUC(0-INF)/D AND T½.
NC = NOT CALCULABE

FIGURE 7

COMPOUND, COMPOSITION AND USES THEREOF

CLAIM OF PRIORITY

This application is a continuation application claiming priority to co-pending U.S. non-provisional patent application Ser. No. 13/649,094 titled COMPOUND, COMPOSITION AND USES THEREOF filed on Oct. 10, 2012, which claimed priority to Ser. No. 13/152,864, filed on Jun. 3, 2011, India Provisional Patent Application No. 3947/CHE/2012, filed on Sep. 24, 2012 and is the national phase application of PCT application No. PCT/IN/2012/000668 filed on Oct. 9, 2012. These applications are hereby incorporated by reference in all of their entireties for all of their teachings.

FIELD OF TECHNOLOGY

This disclosure generally relates to compounds and compositions for the treatment of metabolic conditions, cystinosis, non-alcoholic steatohepatitis, hypertriglyceridemia and neurodegenerative diseases. More particularly, this invention relates to treating subjects with a pharmaceutically acceptable dose of compounds, crystals, esters, amides, salts, hydrates, prodrugs, or mixtures thereof.

BACKGROUND

Metabolism is the process the body uses to get or make energy from proteins, carbohydrates and fats. Cystinosis is a disorder in which the body accumulates the amino acid cystine (a building block of proteins) within cells. Excess cystine forms crystals that can build up and damage cells. These crystals negatively affect various systems in the body, especially the eyes, spleen, liver, bone marrow and kidneys. Cystinosis is an autosomal recessive disorder, caused by mutations of the lysosomal cystine carrier cystinosin, encoded by the CTNS gene (17p13). The concomitant intralysosomal cystine accumulation leads to multi-organ damage, with kidneys being the first affected and later spleen, eyes, liver and bone marrow. Altered mitochondrial oxidative phosphorylation has been demonstrated in animal proximal tubules loaded with cystine dimethyl ester, mimicking cystine accumulation in cystinosis, but has not been confirmed in cells of patients with cystinosis.

Non-alcoholic steatohepatitis (NASH) is a liver disease characterized by macrovesicular steatosis, hepatocyte necrosis, inflammation, Mallory bodies, and fibrosis. NASH is closely associated with the metabolic or insulin resistance syndrome. Oxidative stress is believed to play an important role in pathogenesis of NASH. It is likely involved in the progression of disease from steatosis to NASH and potentially cirrhosis. It has been shown that chronic oxidative stress, generated through the oxidation of cytotoxic free fatty acids, can lead to upregulation of cytokines, induction of the liver cytochrome P450 enzyme 2E1, and depletion of hepatic antioxidant concentration.

Neurodegenerative disorders are a heterogeneous group of diseases of the nervous system, including the brain, spinal cord, and peripheral nerves that have much different aetiology. Many are hereditary; some are secondary to toxic or metabolic processes. Free radicals are highly reactive molecules or chemical species capable of independent existence. Generation of highly Reactive Oxygen Species (ROS) is an integral feature of normal cellular function like mitochondrial respiratory chain, phagocytosis and arachidonic acid metabolism. The release of oxygen free radicals has also been reported during the recovery phases from many pathological noxious stimuli to the cerebral tissues. Some of the neurodegenerative disorders include Alzheimer's disease, Huntington's disease, Parkinson's disease and Lateral sclerosis.

Hypertriglyceridemia is a commonly encountered lipid abnormality frequently associated with other lipid and metabolic derangements. The National Cholesterol Education Program recommends obtaining a fasting lipid panel in adults over the age of 20. The discovery of hypertriglyceridemia should prompt an investigation for secondary causes such as high fat diet, excessive alcohol intake, certain medications, and medical conditions (eg, diabetes mellitus, hypothyroidism). In addition, patients should be evaluated for other components of the metabolic syndrome. These include abdominal obesity, insulin resistance, low high-density lipoprotein (HDL), high triglyceride, and hypertension. Hypertriglyceridemia is classified as primary hypertriglyceridemia when there are no secondary causes identified.

Hypertriglyceridemia is a risk factor for pancreatitis and it accounts for 1 to 4% of cases of acute pancreatitis. Although a few patients can develop pancreatitis with triglyceride levels >500 mg/dL, the risk for pancreatitis does not become clinically significant until levels are >1000 mg/dL. More importantly however, hypertriglyceridemia is typically not an isolated abnormality. It is frequently associated with other lipid abnormalities and the metabolic syndrome (abdominal obesity, insulin resistance, low high-density lipoprotein (HDL), high triglyceride, and hypertension), which are linked to coronary artery disease.

Managing acute pathology of often relies on the addressing underlying pathology and symptoms of the disease. There is currently a need in the art for new compositions to treatment of metabolic conditions such as cystinosis, non-alcoholic Steatohepatitis, hypertriglyceridemia and neurodegenerative disorders.

SUMMARY OF INVENTION

The present invention provides compounds, compositions containing these compounds and methods of synthesizing and for using the same to treat, prevent and/or ameliorate the effects of the conditions such as cystinosis, NASH, hypertriglyceridemia, metabolic conditions and neurodegenerative diseases.

The invention herein provides composition comprising of formula I and their pharmaceutical acceptable salts thereof. The invention also provides pharmaceutical compositions comprising one or more compounds of formula I and their intermediates thereof and one or more of pharmaceutically acceptable carriers, vehicles or diluents. These compositions may be used in the treatment of metabolic conditions and neurodegenerative disorders and its associated complications.

In certain embodiments, the present invention relates to the compounds and compositions of formula I, or pharmaceutically acceptable salts thereof,

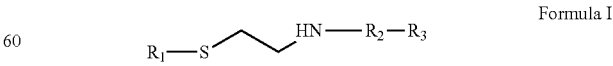

Formula I

Wherein, $R^1$, $R^2$ each independently represents at least one of hydrogen, methyl, amine, cyclohexyl methyl ether, butoxy, propoxy, thiol, alkyl, alkyl thiol, acetyl thiol, acetyl, disulfide, acyl, acylalkyl, alkenyl, alkylthioalkyl, alkynyl, alkoxyaryl, alkoxyalkyl, aryl, aralkyl, aryloxyalkyl, arylthioalkyl, cycloalkyl, ether, ester, amide, heteroaryl, heterocyclyl, lower alkyl, sulfone, sulfoxide, or hydroxyalkyl;

$R^2$ also independently represents at least one of hydrogen, carboxyl, amine, —NH—CO—NH—, —NH—CO—CH$_2$—NH—, —NH—CO—, R—COO—$R^1$, thiol, disulfide,

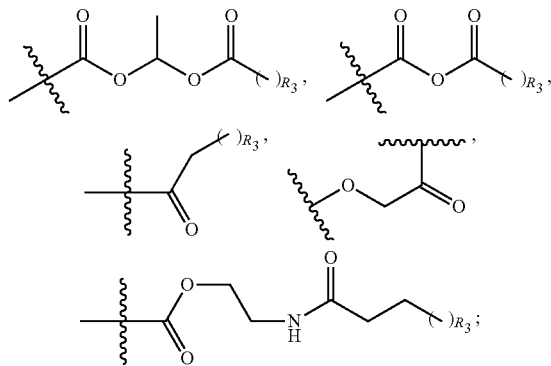

$R^3$ independently represents at least one of

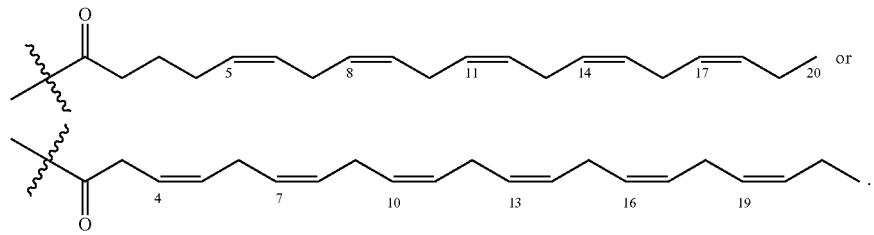

In certain embodiments, the present invention relates to the compounds and compositions of formula 1 or pharmaceutically acceptable salts thereof,

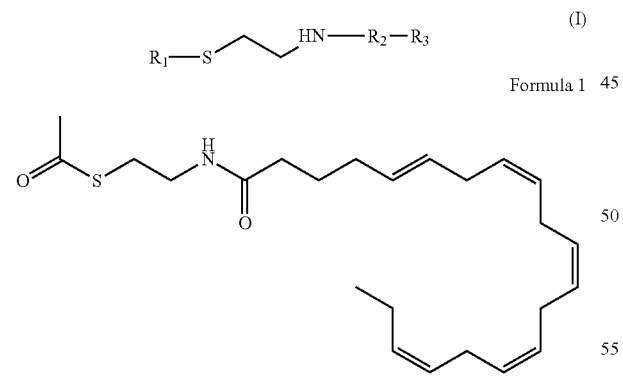

Formula 1

In one embodiment, steps of synthesizing the compounds of formula 1 is described.

Herein the application also provides a kit comprising any of the pharmaceutical compositions disclosed herein. The kit may comprise instructions for use in the treatment of metabolic conditions, non-alcoholic steatohepatitis, neurodegenerative disorder or its related complications.

The application also discloses a pharmaceutical composition comprising a pharmaceutically acceptable carrier and any of the compositions herein. In some aspects, the pharmaceutical composition is formulated for systemic administration, oral administration, sustained release, parenteral administration, injection, subdermal administration, or transdermal administration.

The compositions described herein have several uses. The present application provides, for example, methods of treating a patient suffering from metabolic conditions, non-alcoholic steatohepatitis, neurodegenerative disorders or its related complications manifested from metabolic conditions, chronic diseases or disorders; Hepatology, Hematological, Orthopedic, Cardiovascular, Renal, Skin, Neurological or Ocular complications.

BRIEF DESCRIPTION OF FIGURES

Example embodiments are illustrated by way of example and not limitation in the figures of the accompanying drawings, in which like references indicate similar elements and in which:

FIG. 7: Displays comparative study data of oral administration of KB-ND-002 (Formula 1), Cysteamine or Eicosapentanoiec acid in male mice, concentration versus time profiles were partially evaluable for Pharmacokinetic purposes.

DETAILED DESCRIPTION

Definitions

Figure 1:
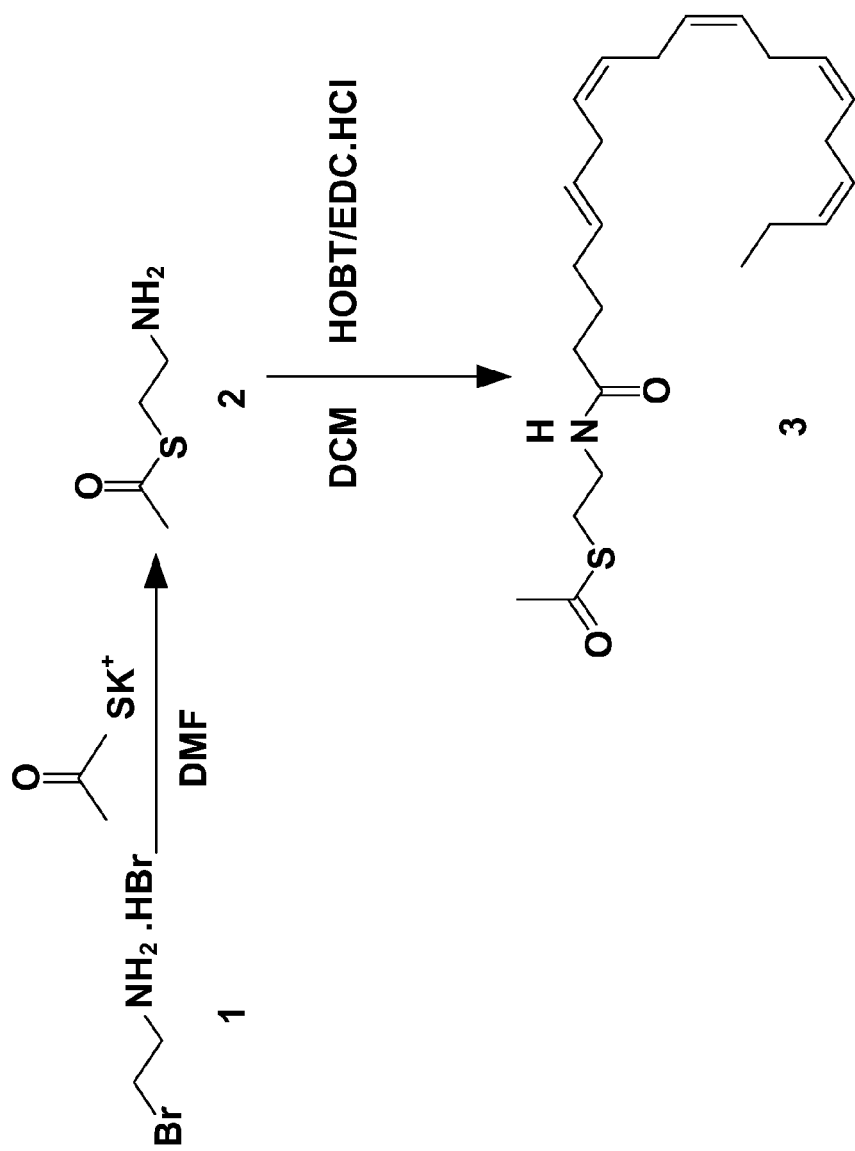
FIG. 1: Illustrates the synthesis of a compound of Formula 1.
Figure 2:
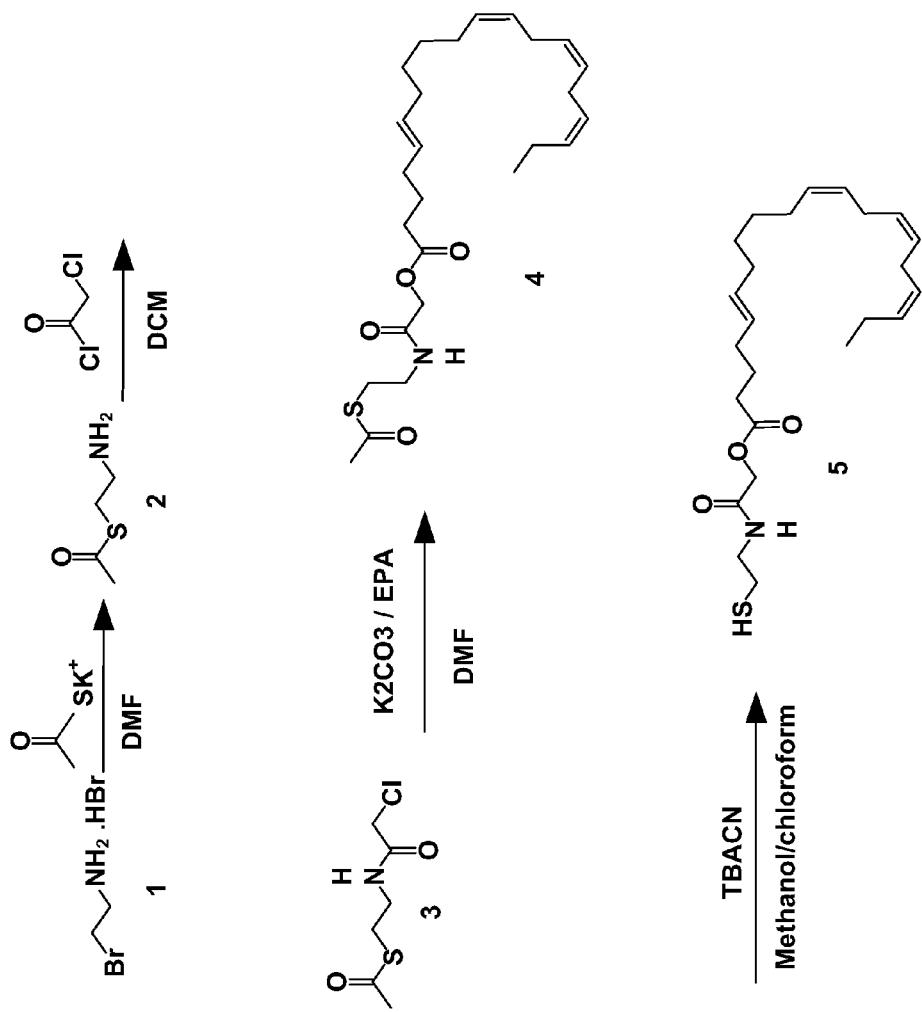
FIG. 2: Illustrates the synthesis of a compound of Formula 2.
Figure 3:
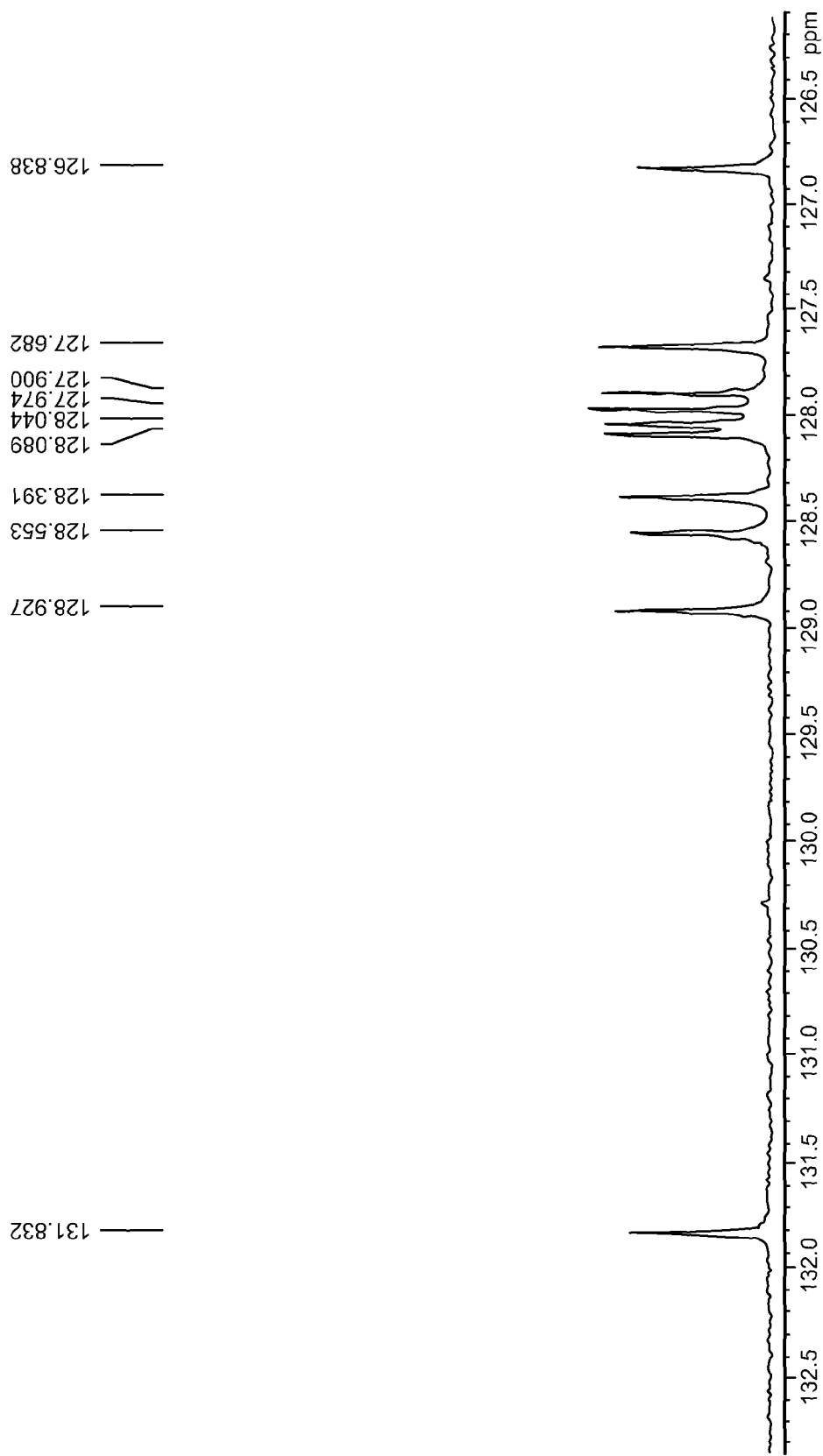
FIG. 3: $C^{13}$ NMR results of a compound of Formula 1.
Figure 4:
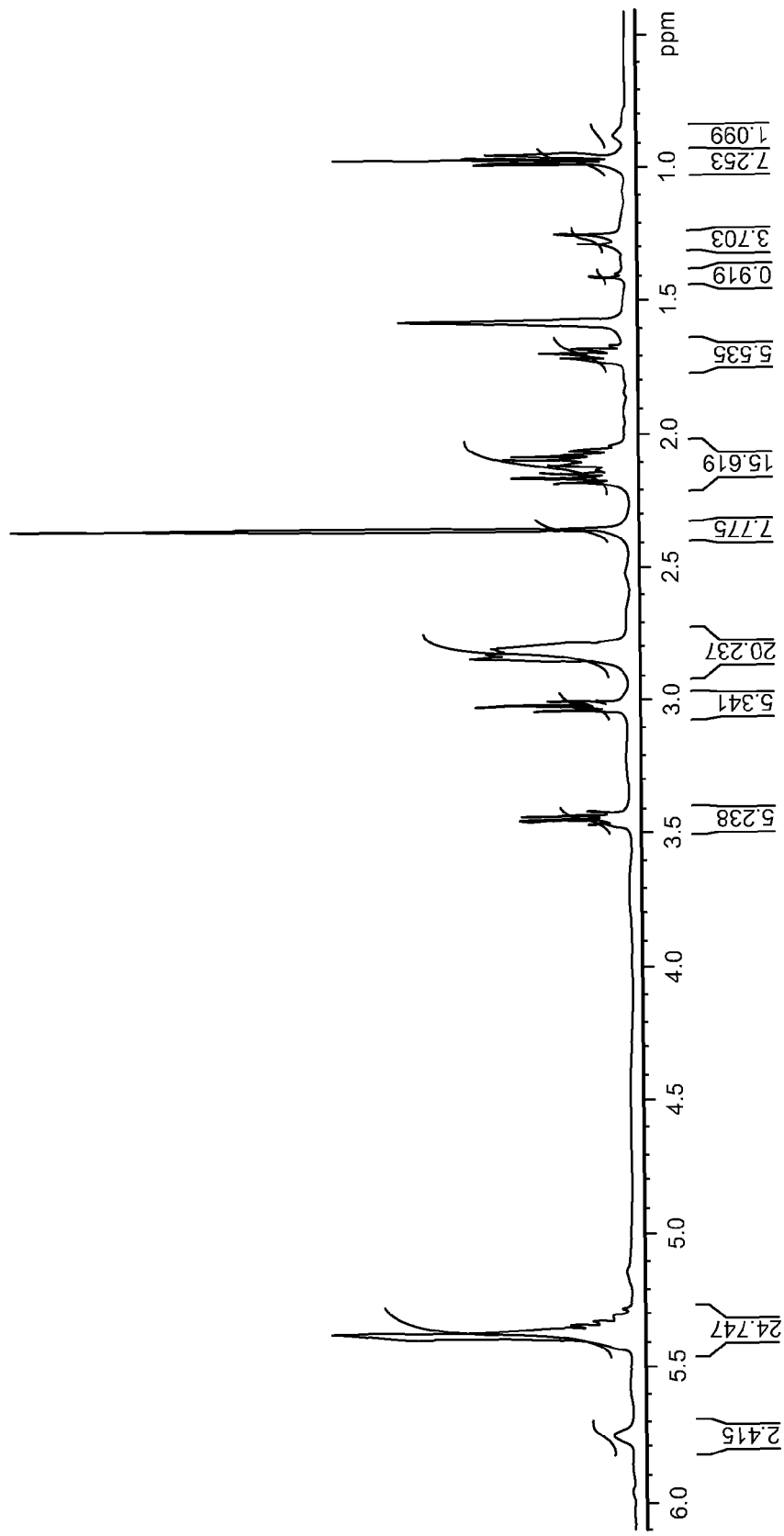
FIG. 4: $H^1$ NMR results of a compound of Formula 1.
Figure 5:
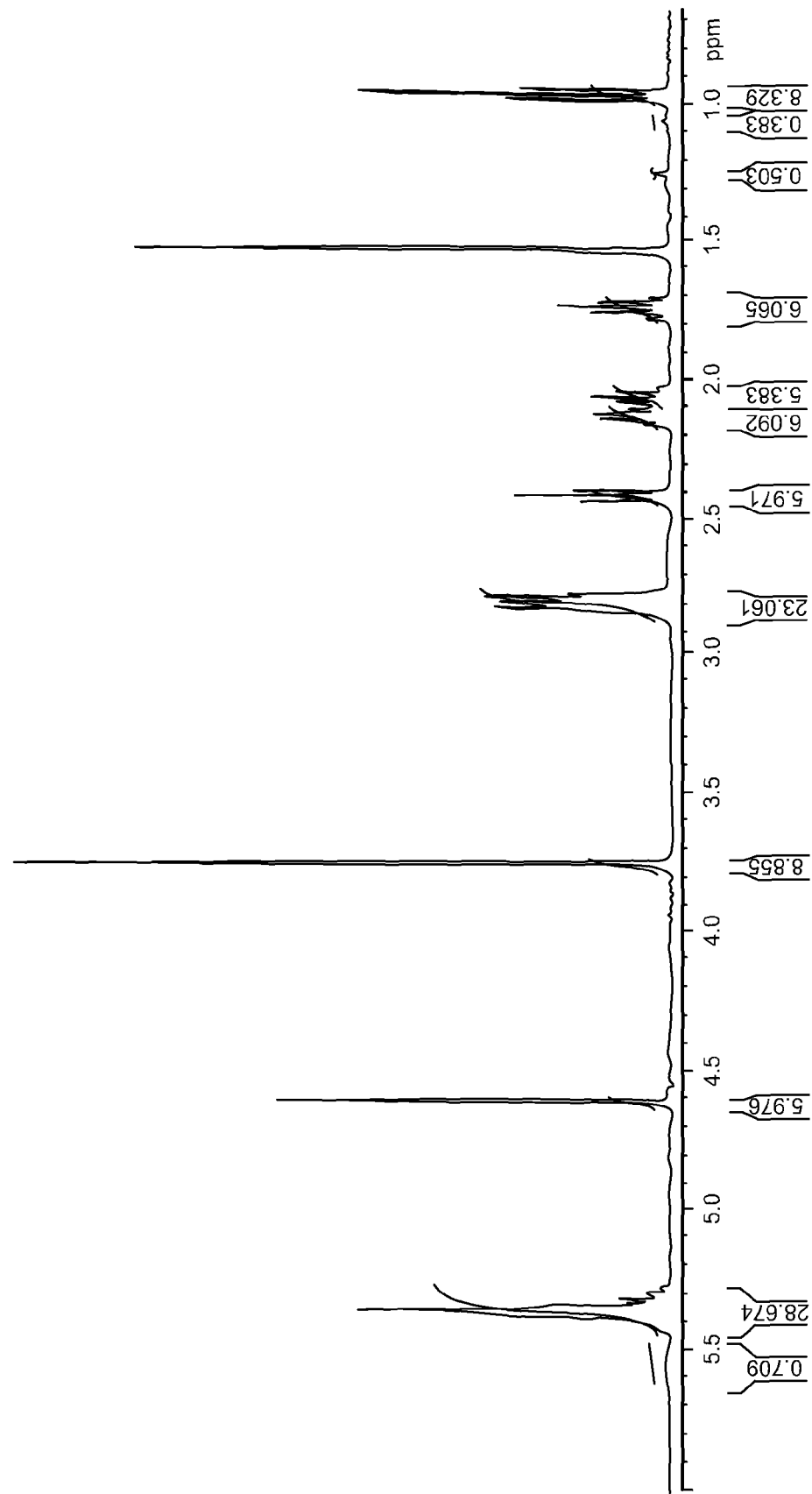
FIG. 5: $H^1$ NMR results of a compound of Formula 2.
Figure 6:
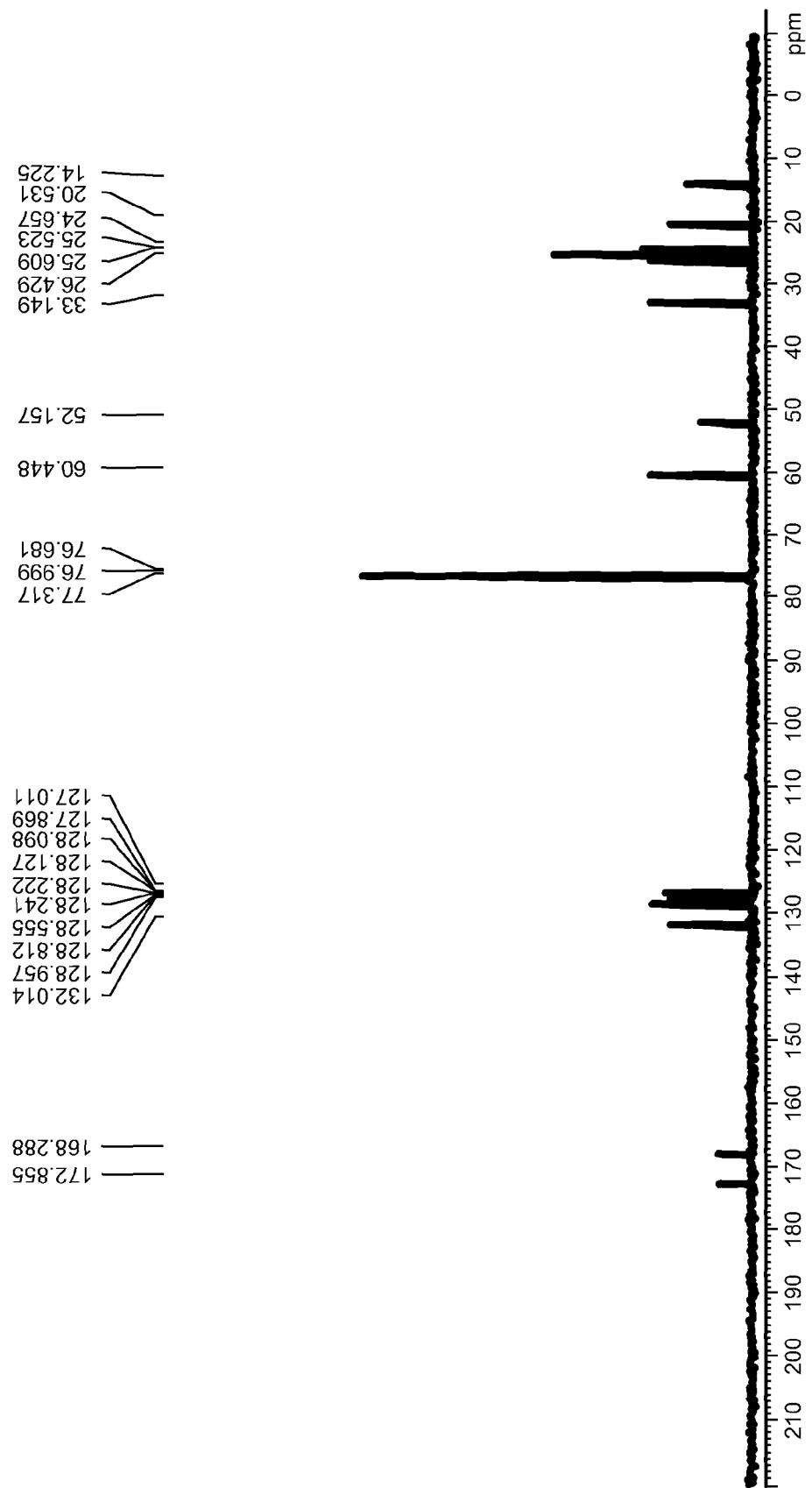
FIG. 6: $C^{13}$ NMR results of a compound of Formula 2.

As used herein, the following terms and phrases shall have the meanings set forth below. Unless defined otherwise, all technical and scientific terms used herein have the same meaning as commonly understood to one of ordinary skill in the art.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure.

The term "alkyl" as used herein refers to a saturated linear or branched-chain monovalent hydrocarbon radical of one to twelve carbon atoms. Examples of alkyl groups include, but are not limited to, methyl (Me, —CH3), ethyl (Et, —CH2CH3), 1-propyl (n-Pr, n-propyl, —CH2CH2CH3), 2-propyl (i-Pr, i-propyl, —CH(CH3)2), 1-butyl (n-Bu, n-butyl, —CH2CH2CH2CH3), 2-methyl-1-propyl (i-Bu, i-butyl, —CH2CH(CH3)2), 2-butyl (s-Bu, s-butyl, —CH(CH3)CH2CH3), 2-methyl-2-propyl (t-Bu, t-butyl, —C(CH3)3), 1-pentyl (n-pentyl, —CH2CH2CH2CH2CH3), 2-pentyl (—CH(CH3)CH2CH2CH3), 3-pentyl (—CH(CH2CH3)2), 2-methyl-2-butyl (—C(CH3)2CH2CH3), 3-methyl-2-butyl (—CH(CH3)CH(CH3)2), 3-methyl-1-butyl (—CH2CH2CH(CH3)2), 2-methyl-1-butyl (—CH2CH(CH3)CH2CH3), 1-hexyl (—CH2CH2CH2CH2CH2CH3), 2-hexyl (—CH(CH3)CH2CH2CH2 CH3), 3-hexyl (—CH(CH2CH3)(CH2CH2CH3)), 2-methyl-2-pentyl (—C(CH3)2CH2CH2CH3), 3-methyl-2-pentyl (—CH(CH3)CH(CH3)CH2CH3), 4-methyl-2-pentyl (—CH(CH3)CH2CH(CH3)2), 3-methyl-3-pentyl (—C(CH3)(CH2CH3)2), 2-methyl-3-pentyl (CH(CH2CH3)CH(CH3)2), 2,3-dimethyl-2-butyl (—C(CH3)2CH(CH3)2), 3,3-dimethyl-2-butyl (—CH(CH3)C(CH3)3,1-heptyl, 1-octyl, and the like.

The term "alkenyl" refers to linear or branched-chain monovalent hydrocarbon radical of two to twelve carbon atoms with at least one site of unsaturation, i.e., a carbon-carbon, sp double bond, wherein the alkenyl radical includes radicals having "cis" and "trans" orientations, or alternatively, "E" and "Z" orientations. Examples include, but are not limited to, ethylenyl or vinyl (—CH=CH2), allyl (—CH2CH=CH2), and the like. The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—C≡CH), propynyl (propargyl, —CH2C≡CH), and the like.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Exemplary substituted alkyls are described below. Cycloalkyls can be further substituted with alkyls, alkenyls, alkoxys, alkylthios, aminoalkyls, carbonyl-substituted alkyls, —CF3, —CN, and the like.

The term "acyl" is art-recognized and refers to a group represented by the general formula hydrocarbylC(O)—, preferably alkylC(O)—.

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. Cx aryl and Cx-Y aryl are typically used where X and Y indicate the number of carbon atoms in the ring.

The term "acylamino" is art-recognized and refers to an amino group substituted with an acyl group and may be represented, for example, by the formula hydrocarbyl C(O)NH—.

The term "acylalkyl" is art-recognized and refers to an alkyl group substituted with an acyl group and may be represented, for example, by the formula hydrocarbyl C(O)alkyl.

The term "acyloxy" is art-recognized and refers to a group represented by the general formula hydrocarbyl C(O)O—, preferably alkyl C(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds.

Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkylamino", as used herein, refers to an amino group substituted with at least one alkyl group.

The term "alkylthio", as used herein, refers to a thiol group substituted with an alkyl group and may be represented by the general formula alkylS-.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. Lower alkyls include methyl and ethyl. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Unless specifically stated as "unsubstituted," references to chemical moieties herein are understood to include substituted variants. For example, reference to an "aryl" group or moiety implicitly includes both substituted and unsubstituted variants.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —CH3. In general, a non-hydrogen substituent may be any substituent that may be bound to an atom of the given moiety that is specified to be substituted. Examples of substituents include, but are not limited to, aldehyde, alicyclic, aliphatic, (Ci-io) alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, (Ci_io) alkoxy, (C4-12) aryloxy, hetero (Ci-io)aryloxy, carbonyl, oxycarbonyl, aminocarbonyl, amino, (Ci-10) alkylamino, sulfonamido, imino, sulfonyl, sulfinyl, (Ci-10) alkyl, halo (Ci-10) alkyl, hydroxy (Ci-10) alkyl, carbonyl (Ci-10) alkyl, thiocarbonyl (Ci_i0) alkyl, sulfonyl (Ci-10) alkyl, sulfinyl (Ci_io) alkyl, (Ci_i0) azaalkyl, imino (Ci-10) alkyl, (C3-12) cycloalkyl (C1-5) alkyl, hetero (C3-12) cycloalkyl (Ci-I0) alkyl, aryl (Ci-I0) alkyl, hetero (Ci-10) aryl (C1-5) alkyl, (C9-12) bicycloaryl (Ci_s) alkyl, hetero (Ce-I2) bicycloaryl (Ci__5) alkyl, (C3-12) cycloalkyl, hetero (C3-12) cycloalkyl, (C9-12) bicycloalkyl, hetero (C3-I2) bicycloalkyl, (C4-I2) aryl, hetero (Ci-10) aryl, (C9-I2) bicycloaryl and hetero (C4-12) bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, (Ci-10) alkoxy, (C4-I2) aryloxy, hetero (Ci-10) aryloxy, carbonyl, oxycarbonyl, aminocarbonyl, amino, (Ci-10) alkylamino, sulfonamido, imino, sulfonyl, sulfinyl, (Ci-10) alkyl, halo (Ci-10) alkyl, hydroxy (Ci-10) alkyl, carbonyl (Ci-10) alkyl, thiocarbonyl (Ci-10) alkyl, sulfonyl (Ci-10) alkyl, sulfinyl (Ci-10) alkyl, (Ci-10) azaalkyl, imino (Ci_io) alkyl, (C3-I2) cycloalkyl (Ci-5) alkyl, hetero (C3-12) cycloalkyl (Ci-10) alkyl, aryl (Ci__10) alkyl, hetero (Ci-io) aryl (Ci__5) alkyl, (C9-I2) bicycloaryl (C1-5) alkyl, hetero (C8-12) bicycloaryl (Ci_s) alkyl, (C3-12) cycloalkyl, hetero (C3__12) cycloalkyl, (C9-12) bicycloalkyl, hetero (C3-12) bicycloalkyl, (C4-12) aryl, hetero (Ci-10) aryl, (C9-12) bicycloaryl and hetero (C4-12) bicycloaryl.

The compounds of the present invention can be present in the form of pharmaceutically acceptable salts. The compounds of the present invention can also be present in the form of pharmaceutically acceptable esters (i.e., the methyl and ethyl esters of the acids of formula 1 to be used as prodrugs). The compounds of the present invention can also be solvated, i.e. hydrated. The solvation can be affected in the course of the manufacturing process or can take place i.e. as a consequence of hygroscopic properties of an initially anhydrous compound of formula 1 (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein, the term "metabolic condition" refers to an Inborn errors of metabolism (or genetic metabolic conditions) are genetic disorders that result from a defect in one or more metabolic pathways; specifically, the function of an enzyme is affected and is either deficient or completely absent. Metabolic condition associated diseases include: Hepatic, Neurologic, Psychiatric, Hematologic, Renal, Cardiovascular, Cancer, Musculoskeletal, Orthopedic and Gastrointestinal.

The term "polymorph" as used herein is art-recognized and refers to one crystal structure of a given compound.

"Residue" is an art-recognized term that refers to a portion of a molecule. For instance, a residue of thioctic acid may be: dihydrolipoic acid, bisnorlipoic acid, tetranorlipoic acid, 6,8-bismethylmercapto-octanoic acid, 4,6-bismethylmercapto-hexanoic acid, 2,4-bismethylmeracapto-butanoic acid, 4,6-bismethylmercapto-hexanoic acid.

The phrases "parenteral administration" and "administered parenterally" as used herein refer to modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intra-articular, subcapsular, subarachnoid, intraspinal and intrastemal injection and infusion.

A "patient," "subject," or "host" to be treated by the subject method may mean either a human or non-human animal, such as primates, mammals, and vertebrates.

The phrase "pharmaceutically acceptable" is art-recognized. In certain embodiments, the term includes compositions, polymers and other materials and/or dosage forms which are, within the scope of sound medical judgment, suitable for use in contact with the tissues of mammals, human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "polymorph" as used herein is art-recognized and refers to one crystal structure of a given compound.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "predicting" as used herein refers to assessing the probability according to which a metabolic condition or neurodegenerative related diseases patient will suffer from abnormalities or complication and/or terminal renal failure and/or death (i.e. mortality) within a defined time window (predictive window) in the future. The mortality may be caused by the central nervous system or complication. The predictive window is an interval in which the subject will develop one or more of the said complications according to the predicted probability. The predictive window may be the entire remaining lifespan of the subject upon analysis by the method of the present invention. Preferably, however, the predictive window is an interval of one month, six months or one, two, three, four, five or ten years after appearance of the cardiovascular complication (more preferably and precisely, after the sample to be analyzed by the method of the present invention has been obtained). As will be understood by those skilled in the art, such an assessment is usually not intended to be correct for 100% of the subjects to be analyzed. The term, however, requires that the assessment will be valid for a statistically significant portion of the subjects to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction will be correct for at least 60%, at least 70%, at least 80%, or at least 90% of the subjects of a given cohort.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the metabolic condition or neurodegenerative disease condition of a subject by administration of an agent even though such agent does not treat the cause of the condition. The term "treating", "treat" or "treatment" as used herein includes curative, preventative (e.g., prophylactic), adjunct and palliative treatment.

Metabolic condition related diseases or disorders includes such as aspartylglusomarinuria, biotinidase deficiency, carbohydrate deficient glycoprotein syndrome (CDGS), Crigler-Najjar syndrome, cystinosis, diabetes insipidus, Fabry, fatty acid metabolism disorders, galactosemia, Gaucher, glucose-6-phosphate dehydrogenase (G6PD), glutaric aciduria, Hurler, Hurler-Scheie, Hunter, hypophosphatemia, 1-cell, Krabbe, lactic acidosis, long chain 3 hydroxyacyl CoA dehydrogenase deficiency (LCHAD), lysosomal storage diseases, mannosidosis, maple syrup urine, Maroteaux-Lamy, metachromatic leukodystrophy, mitochondrial, Morquio, mucopolysaccharidosis, neuro-metabolic, Niemann-Pick, organic acidemias, purine, phenylketonuria (PKU), Pompe, porphyria, pseudo-Hurler, pyruvate dehydrogenase deficiency, Sandhoff, Sanfilippo, Scheie, Sly, Tay-Sachs, trimethylaminuria (Fish-Malodor syndrome), urea cycle conditions, NASH, or any other medical condition, is well understood in the art, and includes administration of a composition which reduces the frequency of, or delays the onset of, symptoms of a medical condition in a subject relative to a subject which does not receive the composition. Neurodegenerative related diseases or disorders includes such as Alzheimer's disease, Amyotrophic lateral sclerosis, Friedreich's ataxia, Huntington's disease, Lewy body disease, Parkinson's disease, Spinal muscular atrophy or any other medical condition, is well understood in the art, and includes administration of a composition which reduces the frequency of, or delays the onset of, symptoms of a medical condition in a subject relative to a subject which does not receive the composition.

The phrase "therapeutically effective amount" is an art-recognized term. In certain embodiments, the term refers to an amount of a salt or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

In certain embodiments, the pharmaceutical compositions described herein are formulated in a manner such that said compositions will be delivered to a patient in a therapeutically effective amount, as part of a prophylactic or therapeutic treatment. The desired amount of the composition to be administered to a patient will depend on absorption, inactivation, and excretion rates of the drug as well as the delivery rate of the salts and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular salt or composition may be adjusted to accommodate variations in the treatment parameters. Such treatment parameters include the clinical use to which the preparation is put, e.g., the site treated, the type of patient, e.g., human or non-human, adult or child, and the nature of the disease or condition.

In certain embodiments, the dosage of the subject compositions provided herein may be determined by reference to the plasma concentrations of the therapeutic composition or other encapsulated materials. For example, the maximum plasma concentration (Cmax) and the area under the plasma concentration-time curve from time 0 to infinity may be used.

The term "solvate" as used herein, refers to a compound formed by solvation (e.g., a compound formed by the combination of solvent molecules with molecules or ions of the solute).

When used with respect to a pharmaceutical composition or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipients may undergo gradual or delayed degradation (e.g., through hydrolysis) with concomitant release of any material incorporated therein, e.g., an therapeutic and/or biologically active salt and/or composition, for a sustained or extended period (as compared to the release from a bolus). This release may result in prolonged delivery of therapeutically effective amounts of any of the therapeutic agents disclosed herein.

The phrases "systemic administration," "administered systemically," "peripheral administration" and "administered peripherally" are art-recognized, and include the administration of a subject composition, therapeutic or other material at a site remote from the disease being treated. Administration of an agent for the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of a salt or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

The present disclosure also contemplates prodrugs of the compositions disclosed herein, as well as pharmaceutically acceptable salts of said prodrugs.

This application also discloses a pharmaceutical composition comprising a pharmaceutically acceptable carrier and the composition of a compound of Formula 1 may be formulated for systemic or topical or oral administration. The pharmaceutical composition may be also formulated for oral administration, oral solution, injection, subdermal administration, or transdermal administration. The pharmaceutical composition may further comprise at least one of a pharmaceutically acceptable stabilizer, diluent, surfactant, filler, binder, and lubricant.

In many embodiments, the pharmaceutical compositions described herein will incorporate the disclosed compounds and compositions (Formulas I) to be delivered in an amount sufficient to deliver to a patient a therapeutically effective amount of a compound of formula 1 or composition as part of a prophylactic or therapeutic treatment. The desired concentration of formula for its pharmaceutical acceptable salts will depend on absorption, inactivation, and excretion rates of the drug as well as the delivery rate of the salts and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular compound of formula 1 may be adjusted to accommodate variations in the treatment parameters. Such treatment parameters include the clinical use to which the preparation is put, e.g., the site treated, the type of patient, e.g., human or non-human, adult or child, and the nature of the disease or condition.

The concentration and/or amount of any compound of formula 1 may be readily identified by routine screening in animals, e.g., rats, by screening a range of concentration and/or amounts of the material in question using appropriate assays. Known methods are also available to assay local tissue concentrations, diffusion rates of the salts or compositions, and local blood flow before and after administration of therapeutic formulations disclosed herein. One such method is microdialysis, as reviewed by T. E. Robinson et al., 1991, microdialysis in the neurosciences, Techniques, volume 7, Chapter 1. The methods reviewed by Robinson may be applied, in brief, as follows. A microdialysis loop is placed in situ in a test animal. Dialysis fluid is pumped through the loop. When compounds with formula 1 such as those disclosed herein are injected adjacent to the loop, released drugs are collected in the dialysate in proportion to their local tissue concentrations. The progress of diffusion of the salts or compositions may be determined thereby with suitable calibration procedures using known concentrations of salts or compositions.

In certain embodiments, the dosage of the subject compounds of formula 1 provided herein may be determined by reference to the plasma concentrations of the therapeutic composition or other encapsulated materials. For example, the maximum plasma concentration (Cmax) and the area under the plasma concentration-time curve from time 0 to infinity may be used.

Generally, in carrying out the methods detailed in this application, an effective dosage for the compounds of Formulas I is in the range of about 0.01 mg/kg/day to about 100 mg/kg/day in single or divided doses, for instance 0.01 mg/kg/day to about 50 mg/kg/day in single or divided doses. The compounds of Formulas I may be administered at a dose of, for example, less than 0.2 mg/kg/day, 0.5 mg/kg/day, 1.0 mg/kg/day, 5 mg/kg/day, 10 mg/kg/day, 20 mg/kg/day, 30 mg/kg/day, or 40 mg/kg/day. Compounds of Formula 1 may also be administered to a human patient at a dose of, for example, between 0.1 mg and 1000 mg, between 5 mg and 80 mg, or less than 1.0, 9.0, 12.0, 20.0, 50.0, 75.0, 100, 300, 400, 500, 800, 1000 mg per day. In certain embodiments, the compositions herein are administered at an amount that is less than 95%, 90%, 80%, 70%, 60%, 50%, 40%, 30%, 20%, or 10% of the compound of formula 1 required for the same therapeutic benefit.

An effective amount of the compounds of formula 1 described herein refers to the amount of one of said salts or compositions which is capable of inhibiting or preventing a disease. For example Metabolic condition associated disease symptoms such as inborn errors of metabolism includes cystinosis, NASH, diabetes and renal and Neurodegenerative diseases include disease symptoms associated to Alzheimer's, Huntingtons disease, Parkinsons disease and lateral sclerosis. An effective amount may be sufficient to prohibit, treat, alleviate, ameliorate, halt, restrain, slow or reverse the progression, or reduce the severity of a complication resulting from nerve damage or demyelization and/or elevated reactive oxidative-nitrosative species and/or abnormalities in neurotransmitter homeostasis's, in patients who are at risk for such complications. As such, these methods include both medical therapeutic (acute) and/or prophylactic (prevention) administration as appropriate. The amount and timing of compositions administered will, of course, be dependent on the subject being treated, on the severity of the affliction, on the manner of administration and on the judgment of the prescribing physician. Thus, because of patient-to-patient variability, the dosages given above are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases.

The compositions provided by this application may be administered to a subject in need of treatment by a variety of conventional routes of administration, including orally, topically, parenterally, e.g., intravenously, subcutaneously or intramedullary. Further, the compositions may be administered intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles.

The compositions may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compositions and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as L-arginine, sodium citrate, calcium carbonate and calcium phosphate may be employed along with various disintegrates such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Appropriate materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof. The compounds of formula 1 may also comprise enterically coated comprising of various excipients, as is well known in the pharmaceutical art.

For parenteral administration, solutions of the compositions may be prepared in (for example) sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The formulations, for instance tablets, may contain e.g. 10 to 100, 50 to 250, 150 to 500 mg, or 350 to 800 mg e.g. 10, 50, 100, 300, 500, 700, 800 mg of the compounds of formula 1 disclosed herein, for instance, compounds of formula 1 or pharmaceutical acceptable salts of a compounds of Formula 1.

Generally, a composition as described herein may be administered orally, or parenterally (e.g., intravenous, intramuscular, subcutaneous or intramedullary). Topical administration may also be indicated, for example, where the patient is suffering from gastrointestinal disorder that prevent oral administration, or whenever the medication is best applied to the surface of a tissue or organ as determined by the attending physician. Localized administration may also be indicated, for example, when a high dose is desired at the target tissue or organ. For buccal administration the active composition may take the form of tablets or lozenges formulated in a conventional manner.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient. For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., ran through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active, ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The tablets of the present invention contain one or more pharmaceutically active agents that are released therefrom upon contact of the tablet with a liquid medium, for example a dissolution medium such as gastrointestinal fluids. "Water soluble," as used herein in connection with non-polymeric materials, shall mean from sparingly soluble to very soluble, i.e., not more than 100 parts water required to dissolve 1 part of the non-polymeric, water soluble solute. See Remington, The Science and Practice of Pharmacy, pp 208-209 (2000). "Water soluble," as used herein in connection with polymeric materials, shall mean that the polymer swells in water and can be dispersed at the molecular level or dissolved in water.

As used herein, the term "modified release" shall apply to tablets, matrices, particles, coatings, portions thereof, or compositions that alter the release of an pharmaceutically active agent in any manner. Types of modified release include controlled, prolonged, sustained, extended, delayed, pulsatile, repeat action, and the like. Suitable mechanisms for achieving these types of modified release include diffusion, erosion, surface area control via geometry and/or impermeable barriers, or other mechanisms known in the art.

In one embodiment of the invention, the first pharmaceutically active agent and the hydrophilic polymer are mixed with a powder containing a pharmaceutically-acceptable carrier, which is also defined herein as the tablet matrix. In one embodiment, the powder has an average particle size of about 50 microns to about 500 microns, such as between 50 microns and 300 microns. Particles in this size range are particularly useful for direct compression processes. In embodiment, the components of powder are blended together, for example as dry powders, and fed into the die cavity of an apparatus that applies pressure to form a tablet core. Any suitable compacting apparatus may be used, including, but not limited to, conventional unitary or rotary tablet press. In one embodiment, the tablet core may be formed by compaction using a rotary tablet press (e.g., such as those commercially available from Fette America Inc., Rockaway, N.J., or Manesty Machines LTD, Liverpool, UK). In general, a metered volume of powder is filled into a die cavity (where the powder is either gravity fed or mechanically fed from a feeder) of the rotary tablet press, and the cavity rotates as part of a "die table" from the filling position to a compaction position. At the compaction position, the powder is compacted between an upper and a lower punch, then the resulting tablet core is pushed from the die cavity by the lower punch and then guided to an injection chute by a stationary "take-off bar.

In one embodiment of the invention, the tablet core may be a directly compressed tablet core made from a powder that is substantially free of water-soluble polymeric binders and hydrated polymers. As used herein, what is meant by "substantially free" is less than 5 percent, such as less than 1 percent, such as less than 0.1 percent, such as completely free (e.g., 0 percent). This composition is advantageous for minimizing processing and material costs and providing for optimal physical and chemical stability of the tablet core. In one embodiment, the density of the tablet core is greater than about 0.9 g/cc.

The tablet core may have one of a variety of different shapes. For example, the tablet core may be shaped as a polyhedron, such as a cube, pyramid, prism, or the like; or may have the geometry of a space figure with some non-flat faces, such as a cone, truncated cone, cylinder, sphere, torus, or the like. In certain embodiments, a tablet core has one or more major faces. For example, the tablet core surface typically has opposing upper and lower faces formed by contact with the upper and lower punch faces in the compression machine. In such embodiments the tablet core surface typically further includes a "belly-band" located between the upper and lower faces, and formed by contact with the die walls in the compression machine.

As discussed above, the tablet core contains one or more hydrophilic polymers. Suitable hydrophilic polymers include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly(ethylene oxide). Examples of suitable acrylic polymers include, but are not limited to, potassium methacrylatedivinylbenzene copolymer, polymethylmethacrylate, high-molecular weight crosslinked acrylic acid homopolymers and copolymers such as those commercially available from Noveon Chemicals under the tradename CARBOPOL™. Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glycolate and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

In one embodiment, an osmogen is incorporated into the tablet core in order to draw water into the tablet upon contact with fluids, such as gastrointestinal fluids. An osmogen as used herein is a water soluble component which preferentially draws water into the tablet core for the purposes of distributing the water throughout the core, so that the active ingredient contained in the core may be released. In one embodiment the osmogen is a salt such as but not limited to sodium chloride, potassium chloride, sodium citrate, or potassium citrate.

The carrier may contain one or more suitable excipients for the formulation of tablets. Examples of suitable excipients include, but are not limited to, fillers, adsorbents, binders, disintegrants, lubricants, glidants, release-modifying excipients, superdisintegrants, antioxidants, and mixtures thereof.

Suitable fillers include, but are not limited to, watersoluble compressible carbohydrates such as sugars (e.g., dextrose, sucrose, maltose, and lactose), starches (e.g., corn starch), sugar-alcohols (e.g., mannitol, sorbitol, maltitol, erythritol, and xylitol), starch hydrolysates (e.g., dextrins, and maltodextrins), and water insoluble plastically deforming materials (e.g., microcrystalline cellulose or other cellulosic derivatives), and mixtures thereof. Suitable adsorbents (e.g., to adsorb the liquid drug composition) include, but are not limited to, water-insoluble adsorbents such as dicalcium phosphate, tricalcium phosphate, silicified microcrystalline cellulose (e.g., such as distributed under the PROSOLV brand (PenWest Pharmaceuticals, Patterson, N.Y.)), magnesium aluminometasilicate (e.g., such as distributed under the NEUSILIN™ brand (Fuji Chemical Industries (USA) Inc., Robinsville, N.J.), clays, silicas, bentonite, zeolites, magnesium silicates, hydrotalcite, veegum, and mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof. Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their salts, such as magnesium stearate and stearic acid, talc, glycerides waxes, and mixtures thereof. Suitable glidants include, but are not limited to, colloidal silicon dioxide. Suitable release-modifying excipients include, but are not limited to, insoluble edible materials, pH-dependent polymers, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof, and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their salts, and mixtures thereof. Examples of suitable fatty acid esters include, but are not limited to, sucrose fatty acid esters, mono-, di-, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof. Examples of super disintegrants include, but are not limited to, croscarmellose sodium, sodium starch glycolate and cross-linked povidone (crospovidone). In one embodiment the tablet core contains up to about 5 percent by weight of such super disintegrant.

Examples of antioxidants include, but are not limited to, tocopherols, ascorbic acid, sodium pyrosulfite, butylhydroxytoluene, butylated hydroxyanisole, edetic acid, and edetate salts, and mixtures thereof. Examples of preservatives include, but are not limited to, citric acid, tartaric acid, lactic acid, malic acid, acetic acid, benzoic acid, and sorbic acid, and mixtures thereof.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, corn, peanut, sunflower, soybean, olive, castor, and sesame oils), glycerol, tetrahydrofuryl alcohol, polyethylene glycols and fatty acid esters of sorbitan, and mixtures thereof.

In some cases, it may be desirable to administer in the form of a kit, it may comprise a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are widely used for the packaging of pharmaceutical unit dosage forms (tablets, capsules, and the like). Blister packs generally consist of a sheet of relatively stiff material covered with a foil of a plastic material that may be transparent. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments the strength of the sheet is such that the tablets or capsules can be removed from the blister pack by manually applying pressure on the recesses whereby an opening is formed in the sheet at the place of the recess. The tablet or capsule can then be removed via said opening.

Method of Synthesis:
Synthesis of Compound of Formula 1:
STEP-1: Reaction of 2-Bromoethylamine Hydrobromide with Potassium thioacetate to obtain compound 2:

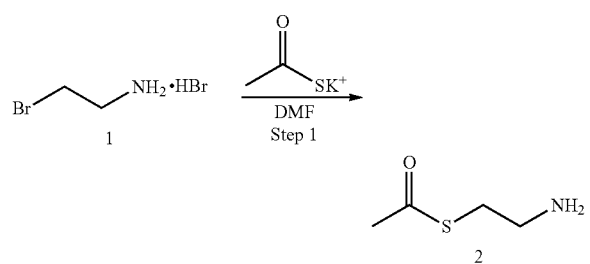

Procedure:

To the solution of 2-Bromoethylamine Hydrobromide (100.0 g, 488 mmol; 1.0 eq) in Dimethylformamide (0.6 L), Potassium thioacetate (55.73 g, 488 mmol; 1 eq) was added at room temperature. The reaction mixture was left stirring for 24 hr at room temperature. On completion of the reaction (monitored by TLC), the solvent was distilled from the reaction mixture completely and Co-distilled with acetonitrile. Acetonitrile was added (1 L) to the reaction mass and warmed up to 85° C. and maintained at 85° C. for 1 hr. The reaction mass was cooled slowly to 0° C. and a white solid was obtained. The white Solid was filtered and washed with acetonitrile (500 mL) to yield 40.0 g (68.9%, based on Potassium thioacetate) of compound 2 as a white solid.

TABLE 1

$^1$H NMR (DMSO-$d_6$, 300 MHz)

| δ | splitting pattern & J value | Protons | Group |
|---|---|---|---|
| 8.01-7.99 | s | 1H | NH$_2$ |
| 3.12-3.05 | m | 2H | CH$_2$ |
| 3.02-2.90 | s | 2H | CH$_2$ |
| 2.38-2.41 | s | 3H | CH$_3$ |

Step 2 for formula 1 amide: Reaction of compound-2 with chloroacetyl chloride to provide compound 3.

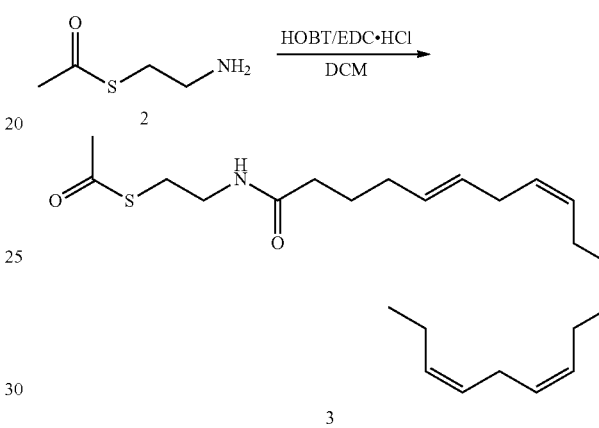

Procedure:

To a 1 L round bottom flask, compound 2 (8 g, 67.1 mmol; 1.0 eq), hydroxybenzotriazole (HOBT, 9 g, 67.1 mmol; 1.0 eq) and Eicosapentaenoic acid (EPA, 20.30 g, 67.1 mmol; 1.0 eq) were mixed with Dimethylformamide (DMF, 200 mL, 25 V, GR grade were added at room temperature, then 1-ethyl-3-(3-dimethylaminopropyl)carbodiimide) (EDCI.HCl, 19.30 g, 100.0 mmol; 1.50 eq) added to it, the reaction mixture was allowed to stir for 4-5 h at RT. Reaction was monitored by TLC. On completion of the reaction, the reaction mixture was diluted with Diethyl ether (2.0 L), washed with water (2×1.0 L) followed by brine solution (1.0 L) and dried over anhydrous Na$_2$SO$_4$ and evaporated under reduced pressure. The crude was purified by column chromatography over 100-200 mesh silica gel by using 10-15% ethyl acetate-hexane to yield 5.0 g (18.5%) of compound 3 as a pale yellow gum.

TABLE 2

$^1$H NMR (CDCl$_3$, 300 MHz) δ:

| δ | splitting pattern & J value | Protons | Group |
|---|---|---|---|
| 5.75 | s | 1H | NH |
| 5.42-5.32 | m | 10H | CH=CH |
| 3.44-3-43 | m | 2H | CH$_2$ |
| 3.10-3.07 | m | 2H | CH$_2$ |
| 2.84-2.76 | m | 8H | 4CH$_2$ |
| 2.45-2.41 | s | 3H | CH$_3$ |
| 2.18-2.04 | m | 6H | 3CH$_2$ |
| 1.58 | m | 2H | CH$_2$ |
| 0.99-0.95 | t = 7.6 Hz | 3H | CH$_3$ |

Carbon Skeletal formula: Molecular formula: $C_{24}H_{37}NO_2S$, Molecular weight: 404.

TABLE 3

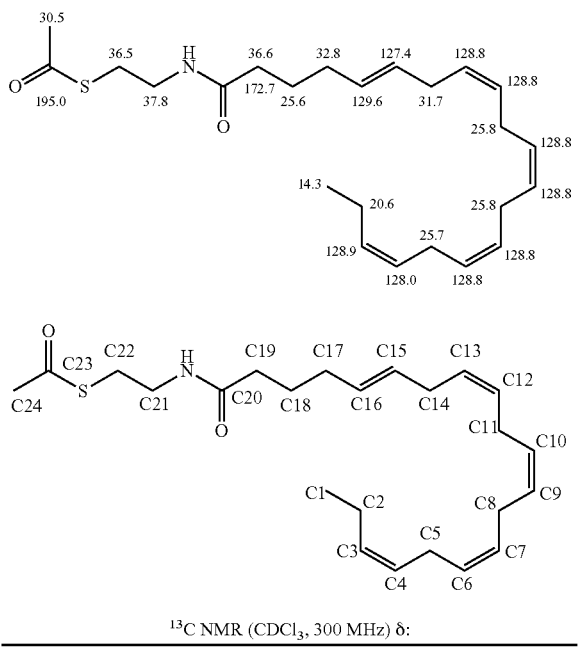

$^{13}$C NMR (CDCl$_3$, 300 MHz) δ:

| δ | Carbon position | Group |
|---|---|---|
| 195.90 | C23 | SCO |
| 172.95 | C20 | NHCO |
| 131.83 | C16 | CH |
| 128.92 | C15 | CH |
| 128.55 | C13 | CH |
| 128.39 | C12 | CH |
| 128.08 | C10 | CH |
| 128.04 | C9 | CH |
| 127.97 | C7 | CH |
| 127.90 | C6 | CH |
| 127.68 | C4 | CH |
| 126.83 | C3 | CH |
| 39.23 | C21 | CH$_2$ |
| 35.75 | C22 | 2CH2 |
| 30.40 | C19 | CH$_2$ |
| 29.48 | C17 | 2CH$_2$ |
| 28.65 | C24 | CH$_3$ |
| 26.49 | C18 | CH$_2$ |
| 25.46 | C14 | CH$_2$ |
| 25.36 | C11, C8 | 2CH$_2$ |
| 25.30 | C5 | CH$_2$ |
| 20.37 | C2 | CH$_2$ |
| 14.08 | C1 | CH3 |

Method of Pharmacokinetic Parameter Estimation

Parameter estimation was performed on mean plasma and brain Eicosapentanoiec acid, KB-ND-002 and Cysteamine concentration vs nominal sampling time values from 3 animals per timepoint. Parameter estimates were derived for each analyte, and matrix using a non-compartmental approach in WinNonlin Enterprise version 5.2.1 (Pharsight Corp., Mountain View, Calif., USA) in accordance with Charles River standard operating procedures. A WinNonlin regression analysis was performed with each concentration vs time profile reviewed by means of visual inspection to appropriately characterise the apparent terminal elimination phase and optimise the reliability of the lambda-z estimation.

Parameter Definitions

| Parameter | Definition of parameter |
|---|---|
| Cmax | The maximum observed mean Eicosapentanoiec acid, KB-ND-002 and Cysteamine concentration after dosing. |
| Cmax/D | The Cmax divided by the dose administered. |
| Tmax | The time after dosing at which the maximum Eicosapentanoiec acid, KB-ND-002 and Cysteamine concentration was observed. |
| AUC(0-t) | The area under the mean Eicosapentanoiec acid, KB-ND-002 and Cysteamine concentration vs time curve from time zero to the time after dosing at which the last quantifiable concentration of the drug was observed (Tlast) estimated by the linear trapezoidal method. |
| AUC(0-t)/D | The AUC(0-t) divided by the dose administered. |
| AUC(0-inf) | The area under the Eicosapentanoiec acid, KB-ND-002 and Cysteamine concentration vs time curve from time zero to infinity: AUC(0-inf) = AUC(0-t) + (Clast/Kel) where Clast = the concentration at time Tlast and Kel = apparent terminal elimination rate constant. |
| AUC(0-inf)/D | The AUC(0-inf) divided by the dose administered. |
| T½ | The apparent terminal elimination half life: T½ = ln 2/Kel; where Kel = apparent terminal elimination rate constant. |
| Rsq | The square of the correlation coefficient for the terminal elimination phase regression line. |

Following Oral Administration of KB-ND-002 (Formula 1), Cysteamine or Eicosapentanoiec Acid in Male Mice, Concentration Vs Time Profiles were Partially Evaluable for PK Purposes.

Eicosapentanoiec Acid

There were no parameter estimates generated for control group animals, however the endogenous Eicosapentanoiec acid concentration data in plasma and brain were reviewed. Concentrations of Eicosapentanoiec acid in control animals were between 5 and 15-fold higher in brain than in plasma. For Groups 1 to 4, maximum concentrations of Eicosapentanoiec acid after dosing increased by approximately 3-fold when compared to endogenous levels in the control group animals in plasma. In brain, Cmaxestimates for Groups 1 to 4 were generally comparable to control animals. In Group 5 however, the difference between endogenous Eicosapentanoiec acid and administered Eicosapentanoiec acid was over 20-fold in plasma. Concentrations of Eicosapentanoiec acid in plasma and brain were quantifiable for the entire duration of sampling of 5 h (Graphs 1 to 4). In Group 5, peak concentrations of Eicosapentanoiec acid were observed 1 h following dosing of 112 mg/kg Eicosapentanoiec acid in both plasma and brain. Systemic exposure to Eicosapentanoiec acid was greatest when 112 mg/kg Eicosapentanoiec acid was administered. Systemic exposure to Eicosapentanoiec acid decreased with increasing doses of KB-ND-002.

KB-ND-002 (Formula I)

Following dosing of KB-ND-002, systemic exposure to KB-ND-002 in plasma (as indicated by Cmaxand AUC(0-t) estimates) increased with increasing dose. Based on the dose normalised estimates of Cmaxand AUC(0-t), this increase was sub-proportional possibly indicating limitations in the absorption of KB-ND-002 at high doses.

In brain, quantifiable concentrations of KB-ND-002 were only evident following the highest dose of KB-ND-002. Systemic exposure to KB-ND-002 observed at this dose level in brain was <1% of that observed in plasma following administration of the low dose of KB-ND-002 (60 mg/kg).

Cysteamine

There were no parameter estimates generated for control group animals, however the endogenous Cysteamine concentration data in plasma and brain were reviewed. Concentrations of Cysteamine in control animals were readily quantifiable in brain than in plasma; between 7 and 12-fold higher in brain than in plasma. For Groups 1, 2, 3 and 5, maximum concentrations of Cysteamine after dosing increased by up to approximately 3-fold when compared to endogenous levels in the control group animals both in plasma and brain. In Group 4 however, the difference between endogenous Cysteamine and administered Cysteamine was over 400-fold in plasma. In brain, the difference between endogenous Cysteamine and administered Cysteamine was up to 10-fold. Concentrations of Cysteamine in brain were quantifiable for the entire duration of sampling of 5 h. However, in plasma, concentrations of Cysteamine were only consistently observed for the entire duration of sampling following administration of Cysteamine (Group 4). In Group 4, peak concentrations of Cysteamine were observed 0.08 h and 0.5 h following dosing of 112 mg/kg Cysteamine in both plasma and brain, respectively. Systemic exposure to Cysteamine was greatest when 112 mg/kg Cysteamine was administered. No further meaningful interpretation of parameter estimates were possible due to Cysteamine being an endogenous substance. Concentrations of Eicosapentanoiec acid in brain were between 1.2 to 2.7-fold higher than Cysteamine.

The present disclosure provides among other things compositions and methods for treating metabolic conditions, cystinosis, non-alcoholic Steatohepatitis, hypertriglyceridemia or neurodegenerative disorders and their complications. While specific embodiments of the subject disclosure have been discussed, the above specification is illustrative and not restrictive. Many variations of the compounds and methods herein will become apparent to those skilled in the art upon review of this specification. The full scope of the claimed compounds and methods should be determined by reference to the claims, along with their full scope of equivalents, and the specification, along with such variations.

What is claimed is:

1. A method of treating at least one of a cardiovascular disease, a hepatic disease, a genetic disorder, and a metabolic disorder comprising:
   administering the compound of Formula 1 to a patient suffering from at least one of a cardiovascular disease, a hepatic disease, a genetic disorder, and a metabolic disorder.

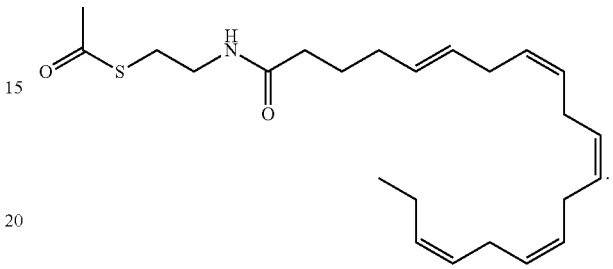

Formula 1

2. The method of claim 1, further comprising administering the compound of comprising Formula 1 through at least one of a non-invasive peroral, a topical ointment, an enteral, a gel solution, a syrup, a lotion, a healing pad, a transmucosal delivery, a targeted delivery, a sustained release delivery, a delayed release delivery, a pulsed release delivery, a patch, and a parenteral delivery.

3. The method of claim 2, wherein the method treats at least one of a hypertriglyceridemia disorder, a stroke, an atrial fibrillation, a coronary heart disease, a non-alcoholic Steatohepatitis, cystinosis, nephropathic cystinosis, and Huntington's disease.

* * * * *